(12) United States Patent
Lischka et al.

(10) Patent No.: US 7,737,232 B2
(45) Date of Patent: Jun. 15, 2010

(54) METHOD FOR THE PRODUCTION OF WATER-FREE RARE EARTH METAL HALOGENIDES, SYNTHESIS MIXTURES CONTAINING WATER-FREE RARE EARTH METAL HALOGENIDES AND USE THEREOF

(75) Inventors: Uwe Lischka, Frankfurt am Main (DE); Jens Röder, Frankfurt am Main (DE); Ulrich Wietelmann, Friedrichsdorf (DE)

(73) Assignee: Chemetall GmbH, Frankfurt am Main (DE)

( * ) Notice: Subject to any disclaimer, the term of this patent is extended or adjusted under 35 U.S.C. 154(b) by 326 days.

(21) Appl. No.: 11/792,804

(22) PCT Filed: Dec. 12, 2005

(86) PCT No.: PCT/EP2005/013285
§ 371 (c)(1),
(2), (4) Date: Sep. 11, 2007

(87) PCT Pub. No.: WO2006/063755
PCT Pub. Date: Jun. 22, 2006

(65) Prior Publication Data
US 2008/0125557 A1    May 29, 2008

(30) Foreign Application Priority Data
Dec. 14, 2004   (DE)   ........................ 10 2004 060 428

(51) Int. Cl.
*C08F 4/44* (2006.01)
(52) U.S. Cl. .................................................. 526/124.3
(58) Field of Classification Search .............. 526/124.3; 502/231
See application file for complete search history.

(56) References Cited

OTHER PUBLICATIONS

Haeberle, "Zur Herstellung Hochreiner Jodide Der Lanthaniden", Technisch-Wissenschaftliche Abhandlungen Der Osram-Gesellschaft, (1973).
Taylor, "Preparation of Anhydrous Lantharion Halides", Chem. Reviews, Amer. Chem. Soc. (1962).
Burgess, et al. "Lanthanide, Yttrium, and Scandium Trihalides: Preparation of Anhydrous Materials and Solution Thermochemistry", Advances in Inorganic Chemistry and Radiochemistry, Aca. Press (1981).
Meyer, "The Ammonium Chloride Route to Anhydrous Rare Earth Chlorides-The Example of YCL3", Inorganic Syntheses, (1989).
Meyer, et all, "The Ammonium-Bromide Route to Anhydrous Rare Earth Bromides MBR3", Journal of the Less-Common Metals, (1987).

*Primary Examiner*—Ling-Siu Choi
*Assistant Examiner*—Sonya Wright
(74) *Attorney, Agent, or Firm*—Fulbright & Jaworski LLP

(57) ABSTRACT

A method for the production of water-free rare earth metal halogenides by reacting rare earth metal oxides with a halogentation agent.

32 Claims, No Drawings

METHOD FOR THE PRODUCTION OF WATER-FREE RARE EARTH METAL HALOGENIDES, SYNTHESIS MIXTURES CONTAINING WATER-FREE RARE EARTH METAL HALOGENIDES AND USE THEREOF

This is a §371 of PCT/EP2005/013285 filed Dec. 12, 2005, which claims priority from German Patent Application No. 10 2004 060 428.2 filed Dec. 14, 2004.

The invention relates to a method for the production of anhydrous rare-earth metal halides, synthesis mixtures containing anhydrous rare-earth metal halides and the use thereof.

Rare-earth metal halides ($REHal_3$ where RE=scandium, yttrium, lanthanum and lanthanoids (Pr, Nd, Pm, Sm, Eu, Gd, Tb, Dy, Ho, Er, Tm, Yb, Lu) and Hal=Cl, Br or I) are used in anhydrous form as reagents in organic synthesis or they serve as starting compounds for the production of further rare-earth compounds such as rare-earth alkoxides or rare-earth organyls. For example, starting from the THF complex of neodymium chloride, allyl neodymium compounds are produced which find use as catalysts for stereospecific butadiene polymerisation (EP 919 573, R. Taube et al., *J. Organomet. Chem.* 1 (513), 37-47, 1996).

Rare-earth metal halides are produced most easily by reacting the oxides with aqueous acids. Solutions of the rare-earth metal halides are obtained in this way, from which the halide salts can be obtained in the form of their crystalline aquo complexes by cooling and/or evaporation. The anhydrous halides cannot be obtained directly from these hydrates, however, as they give off hydrogen halide as well as water when heated and are converted into oxygen-containing solids such as halide oxides or even the pure oxides (this applies to $(ScCl_3)_{aq}$ for example):

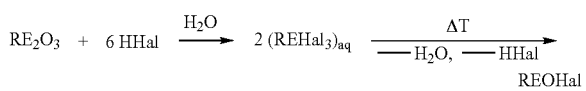

Only under very gentle conditions and in a few cases can anhydrous halides be prepared from the hydrates under purely physical drying conditions. To this end the hydrate compound must first be heated under a stream of hydrogen halide gas (HHal) whilst following a precise temperature regime. For example, anhydrous $NdCl_3$ is obtained by holding $NdCl_3.6H_2O$ under reduced pressure in an HCl atmosphere, initially at 80° C. until most of the water has been driven off, then at 160° C. for 2 to 3 hours and finally at 250° C. The HCl is then replaced by dry nitrogen and cooled. After dehydration the product, which still contains residual oxygen, is purified by vacuum sublimation at 1000 K (Gmelins Handbook of Inorg. Chem., 8$^{th}$ ed., Sc, Y, La—Lu, Part C4b, p. 156). The disadvantages of this method are the expensive apparatus (resistance to corrosion at high temperatures), the complex process per se and the long synthesis times.

For that reason alternative production methods have been developed, which are described briefly below.

Anhydrous chlorides can be prepared by heating the oxides or carboxylic acid salts (e.g. the oxalates) with ammonium chloride:

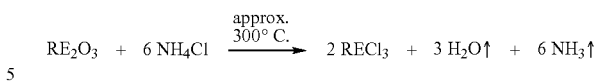

The disadvantages are the high temperatures and the formation of a gaseous, corrosive by-product ($NH_3$).

Instead of ammonium chloride, other chlorinating agents such as $S_2Cl_2$ or $Cl_2/S_2Cl_2$ mixtures can also be used. In this case too, the synthesis as follows $$4RE_2O_3+3S_2Cl_2+9Cl_2 \rightarrow 8RECl_3+6SO_2\uparrow$$

requires high temperatures (500 to 1000° C.) and a toxic, corrosive by-product is formed. $SOCl_2$ can also be used in a similar way (Gmelin C4a, p. 56-58).

Tetrachloromethane and $CCl_4/Cl_2$ mixtures are also capable of chlorinating rare-earth metal oxides at high temperatures:

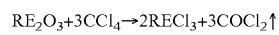

As with the synthesis variants mentioned above, high temperatures (500 to 700° C.) are required and undesirable by-products form (Gmelin C4a, 58-59). The same is also true of the other known chlorinating agents, namely $PCl_5$ and amine hydrochlorides (Gmelin C4a, p. 59-60).

An object of the present invention is to present a method for producing anhydrous rare-earth metal halides $REHal_3$ which avoids the disadvantages of the methods known hitherto and in particular yields the anhydrous halide salts $REHal_3$ directly from the rare-earth metal oxides under gentle reaction conditions (in other words under normal pressure and at ≦approx. 150° C.) and without the formation of corrosive or toxic by-products.

The object is achieved by a method in which rare-earth metal oxides are reacted with halogenating agents having the general formula

where
  M=Si, Ge, Sn, Ti, Zr, Hf
  Hal=Cl, Br, I
  $X^1$, $X^2$, $X^3$=mutually independently Cl, Br, I, H, alkoxy (—OR), wherein R represents an organic radical having 1-20 C atoms, alkyl having 1-20 C atoms or aryl having 6-20 C atoms, wherein the alkyl or aryl radicals can bear one or more further halogen substituents selected from the group comprising F, Cl, Br or I in an aprotic, polar solvent.

M in this formula is always tetravalent.

Preferred halogenating agents are the tetrahalogen compounds $MHal_4$ (M and Hal=meanings given above); $C_6H_5MHal_3$; $HMHal_3$; $C_6H_4HalMHal_3$ where $C_6H_4Hal$=e.g. chlorine, bromine or iodine phenyl; $(H_3C)_2MClCH_2Hal$; $(CH_3)_2MHal_2$; $(CH_3)_3MHal$ or mixtures thereof. Particularly preferred halogenating agents are: $SiCl_4$, $SiBr_4$, $GeCl_4$, $SnCl_4$, $TiCl_4$, $TiBr_4$, $C_6H_5SiCl_3$, $4-ClC_6H_4SiCl_3$, $4-BrC_6H_4SiCl_3$, $HSiCl_3$, $(H_3C)_2ClSiCH_2Cl$, $(H_3C)_2ClSiCH_2Br$, $(CH_3)_2SiCl_2$ or $(CH_3)_3SiCl$.

Ethereal compounds can be used as polar, aprotic solvents. These can be
  open-chain, such as $R^1$—O—$R^2$ (where $R^1$ and $R^2$ are mutually independently alkyl or aryl having 1 to 8 C atoms); or cyclic, such as

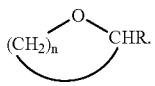

(where n=3 or 4 and R=H or alkyl having 1 to 8 C atoms); or polyfunctional, such as R—O—(—CH$_2$—CH$_2$—O)$_n$—R' (where R and R' are mutually independently alkyl radicals having 1 to 8 C atoms and n=1 to 100), and used either in pure form or as a mixture.

Tetrahydrofuran, tetrahydropyran, 2-methyltetrahydrofuran, dimethyl ether, diethyl ether or methyl tert-butyl ether or a mixture thereof, for example, can be used as the ethereal solvent.

The following aprotic, polar solvents can also be used:

esters, e.g. carboxylic acid esters (such as ethyl acetate, γ-butyrolactone, methyl benzoate), or carbonic acid esters (such as dimethyl carbonate, diethyl carbonate, propylene carbonate, ethylene carbonate), or mixtures thereof; or ketones (e.g. acetone, propionone); or amides (e.g. N-methyl pyrrolidone, dimethyl acetamide, NMPU); or nitriles (e.g. acetonitrile, butyronitrile); or halogen-free sulfur compounds (e.g. dimethyl sulfoxide); or tertiary amines (e.g. triethylamine, tetramethyl ethylene diamine).

One or more hydrocarbons, such as e.g. alkanes (e.g. pentane, hexane, cyclohexane, methyl cyclohexane, heptane or octane) or aromatics (e.g. benzene, toluene, ethyl benzene, cumene or xylene) in the weight ratio of solvent to hydrocarbon of 1:maximum 5, can optionally be added to the polar, aprotic solvents.

The compounds RE$_2$O$_3$, where RE=scandium, yttrium, La, Pr, Nd, Pm, Sm, Eu, Gd, Tb, Dy, Ho, Er, Tm, Yb or Lu, generally in commercial form, are used as rare-earth metal oxides. They are preferably used in powdered form and anhydrously, in other words with H$_2$O contents of <0.5%. Nd$_2$O$_3$, Sm$_2$O$_3$ or La$_2$O$_3$ are particularly preferably used.

Surprisingly it was found that the above-mentioned rare-earth oxides in the form of a suspension in polar aprotic solvents react with the halogenating agents having formula (1) at temperatures as low as ≦30° C., for example, and yield the desired rare-earth metal halides in accordance with the reaction below:

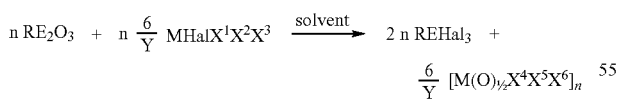

X$^1$, X$^2$, X$^3$ are mutually independently Cl, Br, I, H, alkoxy (—OR), wherein R represents an organic radical having 1-20 C atoms, alkyl having 1-20 C atoms or aryl having 6-20 C atoms, wherein the alkyl or aryl radicals can bear one or more further halogen substituents selected from the group comprising F, Cl, Br or I.

Y can assume the value 1, 2, 3 or 4 and is calculated from the number of halide atoms in the compound MHalX$^1$X$^2$X$^3$: Y=1+(number of substituents X$^1$, X$^2$, X$^3$ denoting halogen).

If none of the substituents X$^1$, X$^2$ and X$^3$ is a halogen, then Y=1; if all the substituents X$^1$, X$^2$ and X$^3$ are a halogen, then Y=4.

In the reaction product [M(O)$_{1/2}$X$^4$X$^5$X$^6$]$_n$ the meaning of the radicals X$^4$, X$^5$ and X$^6$ is as follows:

For each substituent X$^1$, X$^2$ and/or X$^3$ of the halogenating agent that denotes a halogen (Cl, Br, I), the corresponding substituent X$^4$, X$^5$ and/or X$^6$ in the reaction product [M(O)$_{1/2}$X$^4$X$^5$X$^6$]$_n$ consists formally of half an oxygen atom (O)$_{1/2}$. This means that if X$^1$=halogen, then X$^4$=(O)$_{1/2}$, if X$^2$=halogen, then X$^5$=(O)$_{1/2}$ and if X$^3$=halogen, then X$^6$=(O)$_{1/2}$.

For each substituent X$^1$, X$^2$ and/or X$^3$ of the halogenating agent that does not denote a halogen (Cl, Br, I), the corresponding substituent X$^4$, X$^5$ and/or X$^6$ in the reaction product [M(O)$_{1/2}$X$^4$X$^5$X$^6$]$_n$ is unchanged. This means that if X$^1$≠halogen, then X$^4$=X$^1$; if X$^2$≠halogen, then X$^5$=X$^2$; and if X$^3$≠halogen, then X$^6$=X$^3$.

The above reaction equation gives the following theoretical stoichiometries for the various metal halide compounds MHalX$^1$X$^2$X$^3$:

| X$^1$ | X$^2$ | X$^3$ | theoretical molar ratio RE$_2$O$_3$:MHalX$^1$X$^2$X$^3$ |
|---|---|---|---|
| ≠Hal | ≠Hal | ≠Hal | 1:6 |
| =Hal | ≠Hal | ≠Hal | 1:3 |
| =Hal | =Hal | ≠Hal | 1:2 |
| =Hal | =Hal | =Hal | 1:1.5 |

≠Hal means "substituent not equal to halogen";
=Hal means "substituent equal to halogen"

It is sensible to maintain the theoretical reaction conditions to a large extent. In order to bring about a complete conversion to the rare-earth halide even in the case of poorly reactive raw material combinations, however, it is often sensible to use the metal halide compound in excess. In a preferred embodiment the metal halide compound is used in a 1 to 50% excess, based on the theoretical stoichiometries given in the table above.

Two examples of the general reaction equation described above are provided below:

a) X$^1$, X$^2$ and X$^3$=Hal

b) X$^1$=C$_6$H$_5$, X$^2$ and X$^3$=Hal

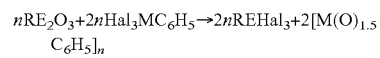

The simple mode of formation of the desired rare-earth metal halides is surprising because the reverse reaction in the absence of the solvent used in the method according to the invention is known from the literature. Thus Gmelin, Sc, Y, La—Lu, C4a, p. 152, describes how quartz and silicate glasses react with liquid and solid rare-earth metal chlorides at elevated temperatures according to the following equation:

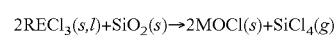

A large number of oxide silicates and chlorosilicates (e.g. Yb$_3$(SiO$_4$)$_2$Cl) were also able to be formed.

By contrast, it was found here that rare-earth metal oxides with silicon tetrachloride, for example, in an aprotic, polar solvent (e.g. tetrahydrofuran (THF)) react quickly and irreversibly even at room temperature to form the desired rare-earth chlorides:

$$2\,RE_2O_3 + 3\,SiCl_4 \xrightarrow{THF} 4\,(RECl_3)_{THF} + 3\,SiO_2$$

The preferred reaction temperature is governed by the reactivity of the individual raw material combination. It is generally possible to work at room temperature. The reaction heat that is formed is dissipated by means of appropriate cooling. With specific raw material combinations, however, it may also be advisable to perform the reaction at low temperatures or in a heated environment. The internal temperature can be between −20 and 100° C., particularly preferably between 0 and 70° C.

It is also particularly surprising that the metal oxide that is formed as a by-product, e.g. $SiO_2$, initially occurs in soluble form, presumably as a metastably soluble polymer sol, in other words in a colloidal distribution. By contrast, the rare-earth metal halides have only a low solubility in the solvents or solvent blends used according to the invention, which means that the rare-earth metal halide in solid form, usually as a solvate with the aprotic polar solvent used, can be isolated in pure form by solid/liquid separation.

For example, in the reaction of $Nd_2O_3$ with $SiCl_4$ in THF, an $NdCl_3.2$ THF complex is formed which is only slightly soluble in THF (approx. 1 to 1.5 wt. % based on $NdCl_3$) and which can be separated off in crystalline form by filtering the solvent and the $SiO_2$ sol and—depending on the precise reaction and processing conditions—isolated with yields of between approx. 60 and 90%.

It is often observed that the $MO_2$ by-product is dissolved as a sol for only a certain time (hours up to a few days) and then converts into gel form. Since a simple separation of the $MO_2$ by-product (e.g. by filtration, decantation or centrifuging) is no longer possible then, a particularly preferred embodiment of the present invention involves performing the solid/liquid separation before the conversion to the gel state.

Reaction mixtures in which the $MO_2$ by-product is already present in gel form can be processed by one of the methods described below, however:
a) separation of the $MO_2$ polymer by osmosis, i.e. membrane permeation, and/or
b) evaporation of the reaction mixture until dry and selective dissolution of the rare-earth metal halide.

For variant a), the $MO_2$-containing reaction mixture in sol or gel form should be purified by filtration through a semi-permeable membrane, i.e. a membrane filter suitable for filtration and having a pore size of between 1 and 100 nm. Whilst the low-molecular-weight, soluble $MHal_3$ complex in dissolved form can pass through the pores, the $MO_2$ polymer is held back.

In variant b) the reaction mixture is partly or wholly evaporated in a temperature range of between 20 and 100° C., preferably under reduced pressure at the end. The remaining suspension or solid reaction mixture is then treated with a solvent which selectively dissolves the rare-earth metal halide. Suitable solvents here are, for example, ethers, alcohols, esters, ketones, amides, nitrites and amines and in principle also water. The latter is disadvantageous, however, because only rare-earth metal hydrates which can be converted back to the anhydrous compounds again by known means—albeit via a circuitous route—can be obtained in this way.

It was surprisingly also found that after total evaporation, the metal oxides formed as by-products no longer dissolve in pH-neutral solvents, i.e. ethers, alcohols, esters, ketones, nitrites, hydrocarbons, either in pure form or as a blend, so the rare-earth metal halides cannot be purified effectively by selective dissolution of the rare-earth halide in these solvents.

The process of extracting the soluble rare-earth metal component can take place in various ways by known methods:
repeated suspension in the pH-neutral solvent and solid/liquid separation until no rare-earth metal compound can be detected in the filtrate
extraction with boiling pH-neutral solvent, e.g. in a Soxhlet apparatus or extractor, or
fixed-bed extraction, i.e. introducing the solid reaction mixture into a type of column and allowing a pH-neutral solvent to pass through it.

Organic solvents from the groups comprising ethers, alcohols, esters, ketones, nitrites and hydrocarbons, either in pure form or as a blend, are particularly suitable as pH-neutral solvents.

If the purity requirements are particularly high, the rare-earth metal halide/metal oxide mixture can also be purified by sublimation at ≧800° C. under high vacuum. Whilst the rare-earth metal halide is volatile under these conditions, the oxide by-product is retained.

The rare-earth metal halides produced by the method according to the invention can be used as starting materials for the production of specific rare-earth metal compounds, such as rare-earth metal alkoxides, rare-earth metal amides and rare-earth metal alkyls and aryls, especially of cyclopentadiene compounds and compounds of benzoannelated cyclopentadiene derivatives such as indene or fluorene compounds. They can also be used directly as Lewis-acid catalysts in organic and inorganic synthesis chemistry.

Since the neutral metal oxide by-products have a non-disruptive effect on many reactions, the reaction or synthesis mixtures can also be used directly, i.e. without a prior purification stage, as reagents or catalysts. For cost reasons it is particularly preferably to produce the rare-earth halide compound in situ and to use it directly "in the same pot" for a subsequent chemical step, such as e.g. acetalisations, Friedel-Crafts reactions, etc.

The rare-earth metal halides produced according to the invention can be used for example as a reagent or catalyst for organic or inorganic reactions, as a raw material for the production of specific rare-earth compounds or as a catalyst in polymerisation reactions, for example in the production of polyolefins (polyethylene, polypropylene, EPDM and SBS copolymers) or in condensation polymerisation for the synthesis of polyesters such as polyethylene terephthalate, polyethylene naphthenate or polybutylene terephthalate.

The metal halide compounds are particularly preferably used for one of the following reactions: condensation reactions, aldol reactions, acetal formation, C—C coupling reactions and ring-opening reactions.

The subject-matter of the invention is described in more detail by means of the following examples:

EXAMPLE 1

Production of $NdCl_3 \cdot 2$ THF from $Nd_2O_3/SiCl_4$ in THF 25.2 g (75 mmol) of neodymium oxide (99%, from Aldrich) were suspended in 140 g of THF in an inerted, i.e. dried and argon-filled, 0.5-litre double-jacket reactor with reflux condenser and dropping funnel. 20.5 g (120 mmol) of silicon tetrachloride were metered in with stirring within 30 minutes at internal temperatures of between 25 and 30° C.

The reaction was clearly exothermic and a light blue suspension was formed. On completion of the dropwise addition the mixture was stirred for a further 1.5 hours at approx. 30° C. and then cooled to 20° C.

The suspension was then discharged onto a G3 sintered-glass filter and the crystalline filter residue rewashed once with 48 g of THF.

After vacuum drying for 4 hours at 25° C., 50.8 g of a finely crystalline, free-flowing powder were obtained.

Analysis: 2.65 mmol/g Nd; 7.51 mmol/g Cl; 52 ppm Si (Theoretical for $NdCl_3 \cdot 2$ THF: 2.53 mmol/g Nd; 7.60 mmol/g Cl)

Yield: 90% of theoretical.

After being left to stand for two days, the initially somewhat liquid filtrates converted to gel form.

EXAMPLE 2

Production of $NdCl_3 \cdot 2$ THF from $Nd_2O_3$ and $TiCl_4$/THF in THF Suspension 968 g of a 0.28 molar titanium tetrachloride solution in THF (271 mmol) were placed in a 2-litre double-jacket reactor and 54.5 g (162 mmol) of neodymium oxide powder were added in portions (using a solids metering bulb) with stirring within approx. 40 minutes at internal temperatures of between 25 and 30° C.

After the release of heat had died down, stirring was continued for a further 30 minutes at approx. 25° C. and the suspension was then filtered and the filter residue washed with 150 g of THF. 75.6 g of a powder were obtained after vacuum drying.

Analysis: Nd=2.50 mmol/g, Cl=7.50 mmol/g, Ti=0.05 mmol/g

Yield: 58% of theoretical.

The product contained 0.4 wt. % of $TiO_2$.

After concentration in vacuo, cooling to 0° C. and subsequent filtration, a further 32 g of a powder contaminated with 1.8 wt. % of $TiO_2$ were able to be obtained from the combined filtrates. The total yield was around 83% of theoretical.

Further examples according to the invention can be taken from the following two tables:

TABLE 1

Production of rare-earth halides

| Exp. no. | RE oxide Type | RE oxide Amount (mmol) | Halogenating agent Type | Halogenating agent Amount (g) | Solvent Type | Solvent Amount (g) | Reaction conditions | Processing |
|---|---|---|---|---|---|---|---|---|
| 3 | $Sm_2O_3$ | 19.4 | $SiCl_4$ | 29.4 | THF | 90 | 2 h refluxing | Filtration/washing |
| 4 | $Nd_2O_3$ | 50 | $PhSiCl_3$ | 100 | THF | 92 | 1 h 30° C., then 2 h refluxing | Filtration/washing |
| 5 | $La_2O_3$ | 102 | $SiCl_4$ | 156 | THF | 334 | Stirring approx. 25° C., then 1 h refluxing | Total evaporation/Soxhlet extraction |
| 6 | $La_2O_3$ | 100 | $SiCl_4$ | 158 | THF | 248 | Stirring approx. 25° C., then 3 h refluxing | Filtration/washing |
| 7 | $La_2O_3$ | 50 | $SiCl_4$ | 78.9 | THF/toluene | 160 | As exp. 6 | Filtration/washing |
| 8 | $La_2O_3$ | 50 | $SiCl_4$ | 79 | Acetone | 296 | 3 h 20-50° C. | Filtration/washing |
| 9 | $La_2O_3$ | 50 | $SiCl_4$ | 78.5 | DMC | 171 | 1 h approx. 25° C., then 1.5 h refluxing | Filtration/washing |
| 10 | $La_2O_3$ | 30 | $SiBr_4$ | 45 | 2-MeTHF | 132 | 3 h 25° C., then 1 h refluxing | Filtration/washing |
| 11 | $La_2O_3$ | 50 | $Me_2Si(CH_2Cl)Cl$ | 300 | THF | 120 | 8 h refluxing | Filtration/washing |

TABLE 2

Reaction results for the rare-earth halide syntheses

| | Product | | Analysis (mmol/g) | | | Composition | Yield (% of |
|---|---|---|---|---|---|---|---|
| Exp. no. | Appearance | Amount (g) | RE | Hal | Si | REHal$_3$-n donor | theor.) |
| 3 | light yellow powder | 12.5 | 2.6 (Sm) | 7.3 (Cl) | 0.10 | SmCl$_3$•2 THF | 84 |
| 4 | light blue powder | 36.5 | 2.45 (Nd) | 7.5 (Cl) | 0.05 | NdCl$_3$•2 THF | 89 |
| 5 | white powder | 28 | 2.80 (La) | 8.60 (Cl) | 0.15 | LaCl$_3$•2 THF | 38 |
| 6 | white powder | 47.9 | 2.60 (La) | 7.4 (Cl) | ≦0.05 | LaCl$_3$•2 THF | 62 |
| 7 | " | 31.7 | 2.58 (La) | 7.70 (Cl) | 0.01 | LaCl$_3$•2 THF | 82 |
| 8 | bulky, white | 37.0 | 2.40 (La) | 7.20 (Cl) | 1.80 | LaCl$_3$•2.5 acetone* | 89 |
| 9 | white powder | 27.6 | 2.45 (La) | 6.90 (Cl) | 0.08 | LaCl$_3$•1.6 DMC | 67 |
| 10 | white powder | 9.3 | 1.97 (La) | 5.70 (Br) | 0.02 | LaBr$_3$•2 THF | 31 |
| 11 | white powder | 31 | 2.71 (La) | 8.10 (Cl) | 0.10 | LaCl$_3$•2 THF | 84 |

*contains approx. 8% SiO$_2$

In experiment 3 samarium oxide was used instead of Nd$_2$O$_3$ and SmCl$_3$ in the form of the THF complex was obtained as the reaction product.

In experiment 4 an organo-substituted silyl halide (C$_6$H$_5$SiCl$_3$) was used instead of SiCl$_4$ which after brief refluxing converted neodymium oxide into the chloride.

For examples 5 to 11 powdered lanthanum oxide was used. Experiments 6, 7, 8 and 9 differ from one another in the choice of reaction solvent: THF, THF-toluene, acetone and DMC are similarly suitable. If acetone is used, the by-product SiO$_2$ is precipitated out at the same time as the LaCl$_3$ crystallisate.

In experiment 5 a special processing method was chosen; after reacting the reactants La$_2$O$_3$ and SiCl$_4$ in THF, the reaction suspension formed was totally evaporated in a rotary evaporator at a bath temperature of 60° C. and under a final pressure of 14 mbar. The solid, white residue was ground in an argon-filled glove box and then extracted with boiling THF in a Soxhlet apparatus for approx. 30 hours. A suspension was formed in this way which was filtered after cooling. The solid filter residue was washed with THF and dried at room temperature to constant weight. 28.0 g of a fine white powder were obtained with the composition given in Table 2.

Example 10 shows the production of a rare-earth bromide, in this case LaBr$_3$, which was produced using the brominating agent SiBr$_4$.

Finally, example 11 shows the use of an organosilicon chloride in which the organic radical is itself functionalised (with chloride).

The invention claimed is:

1. A method for producing anhydrous rare-earth metal halides (REHal$_3$), comprising reacting a rare-earth metal oxide of the formula RE$_2$O$_3$, wherein RE is Sc, Y, La, Pr, Nd, Pm, Sm, Eu, Gd, Tb, Dy, Ho, Er, Tm, Yb or Lu, with a halogenating agent of the formula $$MHalX^1X^2X^3 \qquad (1)$$

wherein M is Si, Ge, Sn, Ti, Zr or Hf
Hal is Cl, Br, I
X1, X2 are X3 are each independently Cl, Br, I, H, or alkoxide (—OR), wherein R is an organic radical having 1-20 C atoms, an alkyl having 1-20 C atoms or an aryl having 6-20 C atoms, wherein the alkyl or aryl radicals can be substituted at least once with F, Cl, Br or I,
in an aprotic, polar solvent.

2. A method according to claim 1, wherein the halogenating agent is a tetrahalogen compound of the formula MHal$_4$.

3. A method according to claim 1, wherein the halogenating agent is selected from the group consisting of C$_6$H$_5$MHal$_3$, HMHal$_3$, C$_6$H$_4$HalMHal$_3$, (H$_3$C)$_2$MaCH$_2$Hal, (CH$_3$)$_2$ MHal$_2$ and (CH$_3$)$_3$MHal.

4. A method according to claim 1, wherein the halogenating agent is selected from the group consisting of SiCl$_4$, SiBr$_4$, GeCl$_4$, SnCl$_4$, TiCl$_4$, TiBr$_4$, C$_6$H$_5$SiCl$_3$, 4-ClC$_6$H$_4$SiCl$_3$, 4-BrC$_6$H$_4$SiCl$_3$, HSiCl$_3$, (H$_3$C)$_2$ClSiCH$_2$C, (H$_3$C)$_2$ClSiCH$_2$Br, (CH$_3$)$_2$SiCl$_2$ and (CH$_3$)$_3$SiCl.

5. A method according to claim 1, wherein one or more of the aprotic, polar solvent comprises at least one of an ester, a carbonic acid ester, a ketone, an amide, a nitrile, a halogen-free sulfur compound or a tertiary amine.

6. A method according to claim 1, wherein the solvent comprises at least one of tetrahydrofuran, tetrahydropyran, 2-methyltetrahydrofuran, dimethyl ether, diethyl ether or methyl tert-butyl ether.

7. A method according to claim 1, wherein one or more hydrocarbons are added to the polar, aprotic solvent in the weight ratio of 1 part of polar, aprotic solvent to a maximum of 5 parts of hydrocarbon.

8. A method according to claim 7, wherein the hydrocarbon is at least one of an alkane or an aromatic.

9. A method according to claim 1, wherein the rare-earth metal oxide is in powdered form and has a residual water content of <0.5 wt. %.

10. A method according to claim 1, wherein the rare earth oxide is Nd$_2$O$_3$, Sm$_2$O$_3$ or La$_2$O$_3$.

11. A method according to claim 1, wherein the molar ratio between the rare-earth oxide RE$_2$O$_3$ and the metal halogen compound MHalX$^1$X$^2$X$^3$ is chosen as follows:
approximately 1:6 for X$^1$, X$^2$, X$^3$≠Hal;
approximately 1:3 for X$^1$=Hal, X$^2$, X$^3$≠Hal;
approximately 1:2 for X$^1$, X$^2$=Hal, X$^3$≠Hal; or
approximately 1:1.5 for X$^1$, X$^2$, X$^3$=Hal.

12. A method according to claim 1, wherein the halogenating agent is used in an excess of 1 to 50 mol %.

13. A method according to claim 1, wherein the reaction temperature is in the range from −20 to +100° C.

14. A method according to claim 13, wherein the reaction temperature is in the range from 0 to 70° C.

15. A method according to claim 1, wherein after the end of the conversion but before the start of any gelling process that might begin, the rare-earth metal halide is separated from the solution of the metal oxide by-product by means of a solid/liquid separation.

16. A method according to claim 15, wherein the solid rare-earth metal halide is purified by washing with an aprotic solvent.

17. A method according to claim 16, wherein the purification is on a filter, in a Soxhlet extractor or in a column by fixed-bed extraction.

18. A method according to claim 1, wherein after the exothermic reaction has died down the reaction mixture is evaporated until dry.

19. A method according to claim 18, wherein the evaporation is performed in the temperature range between 20 and 100° C. and at least partly under reduced pressure.

20. A method according to claim 18, wherein the rare-earth halide is obtained from the evaporation residue by extraction with a pH-neutral solvent.

21. A method according to claim 20, wherein the pH-neutral solvent contains one or more substances selected from the group comprising ethers, alcohols, esters, ketones and nitriles and optionally additionally one or more hydrocarbons.

22. A method according to claim 1, wherein the rare-earth metal halide/metal oxide mixture is purified by sublimation at ≧800° C. under high vacuum.

23. The product produced by the process of claim 1.

24. The product produced by reacting a rare-earth oxide of formula $RE_2O_3$, where RE is selected from the group consisting Sc, Y, La, Pr, Nd, Pm, Sm, Eu, Gd, Tb, Dy, Ho, Er, Tm, Yb and Lu, with a halogenating agent selected from the group consisting of $SiCl_4$, $SiBr_4$, $GeCl_4$, $SnCl_4$, $TiCl_4$, $TiBr_4$, $C_6H_5SiCl_3$, 4-$ClC_6H_4SiCl_3$, 4-$BrC_6H_4SiCl_3$, $HSiCl_3$, $(H_3C)_2ClSiCH_2Cl$, $(H_3C)_2ClSiCH_2Br$, $(CH_3)_2SiCl_2$ and $(CH_3)_3SiCl$ in a polar, aprotic solvent or an aprotic solvent blend selected from the group comprising THF, 2-MeTHF, THP, dimethyl ether, diethyl ether, methyl tert-butyl ether, ethyl acetate, γ-butyrolactone, methyl benzoate, dimethyl carbonate, diethyl carbonate, propylene carbonate, ethylene carbonate, acetone, propiophenone, N-methylpyrrolidone, dimethyl acetamide, NMPU, acetonitrile, butyronitrile, dimethyl sulfoxide, triethylamine or tetramethyl ethylene diamine, either in pure form or as a blend.

25. A method comprising adding the reaction mixture according to claim 24 as a reagent or catalyst in an organic or inorganic reaction.

26. A method comprising adding a sufficient amount of the process product produced according to claim 24 as a raw material for producing a specific rare-earth compound or as a catalyst in a polymerization reaction.

27. The method according to claim 26, wherein the polymerization reaction leads to the production of a polyolefin or a polyester.

28. The method according to claim 25, wherein the organic or inorganic reaction is a condensation, aldol reaction, acetal formation, C—C coupling or ring-opening reaction.

29. A method according to claim 1, wherein polar, aprotic solvent comprises at least one of the formula $R^1$—O—$R^2$ wherein $R^1$ and $R^2$ are mutually independently alkyl or aryl having 1 to 8 C atoms; cyclic, where n=3 or 4 and R=H or alkyl having from 1 to 8 C atoms; or polyfunctional, such as R—O—(—$CH_2$—$CH_2$—O)—R', where R and R' are mutually independently alkyl radicals having 1 to 8 C atoms and n is from 1 to 100, and used either in pure form or as a mixture.

30. A method according to claim 29, wherein either of the formula $R^1$—O—$R^2$ wherein at least one of $R^1$ and $R^2$ are

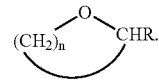

31. A method according to claim 29, wherein said pure form is used.

32. A method according to claim 30, wherein said mixture is used.

* * * * *